United States Patent [19]
Lonsbury et al.

[11] Patent Number: 5,318,032
[45] Date of Patent: Jun. 7, 1994

[54] GUIDING CATHETER HAVING SOFT TIP

[75] Inventors: Michael T. Lonsbury, Sunnyvale; Richard S. Jaraczewski, Livermore; Fred H. Co, Santa Clara, all of Calif.

[73] Assignee: Devices for Vascular Intervention, Redwood City, Calif.

[21] Appl. No.: 831,599

[22] Filed: Feb. 5, 1992

[51] Int. Cl.$^5$ ............................................. A61B 6/00
[52] U.S. Cl. ..................................... 128/658; 604/282
[58] Field of Search ................... 128/658, 657, 656; 604/95, 280, 281, 282, 158, 164, 264; 138/120, 123, 124, 125, 126, 127, 140, 141, 153

[56] References Cited

U.S. PATENT DOCUMENTS

| | | |
|---|---|---|
| 3,416,531 | 12/1968 | Edwards . |
| 3,924,632 | 12/1975 | Cook . |
| 4,425,919 | 1/1984 | Alston, Jr. et al. ................ 128/658 |
| 4,586,923 | 5/1986 | Gould et al. ......................... 604/95 |
| 4,636,346 | 1/1987 | Gold et al. ......................... 264/139 |
| 4,817,613 | 4/1989 | Jaraczewski et al. ............. 128/658 |
| 4,842,590 | 6/1989 | Tanabe et al. ..................... 604/282 |
| 4,863,442 | 9/1989 | De Mello et al. ................. 604/282 |
| 4,899,787 | 2/1990 | Ouchi et al. ....................... 138/131 |
| 5,019,057 | 5/1991 | Truckai ............................... 604/282 |
| 5,045,072 | 9/1991 | Castillo et al. .................... 604/280 |
| 5,057,092 | 10/1991 | Webster, Jr. ...................... 604/282 |
| 5,061,257 | 10/1991 | Martinez et al. .................. 604/282 |
| 5,078,702 | 1/1992 | Pomeranz ........................... 604/280 |
| 5,116,309 | 5/1992 | Coll ....................................... 604/8 |

OTHER PUBLICATIONS

Cook, Inc., Radiology, Cardiology & Surgery Catalog 1982, Author unknown.

*Primary Examiner*—Stephen C. Pellegrino
*Assistant Examiner*—Guy V. Tucker
*Attorney, Agent, or Firm*—Townsend and Townsend Khourie and Crew

[57] ABSTRACT

A vascular guiding catheter comprises an inner tubular member having a torque transmitting member formed over a major portion thereof and a soft polymeric tip formed at the distal end thereof. The torque transmitting member provides the characteristics of torsional stiffness and axial flexibility which are necessary to be able to introduce the catheter to the vascular system. The soft polymeric tip reduces the likelihood that the catheter can injure the blood vessel and provides a convenient location for the inclusion of perfusion ports. A reinforcement layer is provided over a transition region between the termination of the torque transmitting member and the soft distal tip. Optionally, reinforcement layers may be provided elsewhere along the length of the catheter.

35 Claims, 3 Drawing Sheets

GUIDING CATHETER HAVING SOFT TIP

BACKGROUND OF THE INVENTION

1. Field of the Invention

The present invention relates generally to apparatus for inserting and positioning vascular catheters within a patient's vascular system. More particularly, the present invention relates to the construction of a guiding catheter having controlled flexibility and a soft tip.

Arteriosclerosis, also known as atherosclerosis, is a common human ailment arising from the deposition of fatty-like substances, referred to as atheroma or plaque, on the walls of blood vessels. Such deposits occur both in peripheral blood vessels that feed the limbs in the body and coronary blood vessels which feed the heart. When deposits accumulate in localized regions of a blood vessel, blood flow is restricted and the person's health is at serious risk.

Numerous approaches for reducing and removing such vascular deposits have been proposed, including balloon angioplasty where a balloon-tipped catheter is used to dilate a region of atheroma, atherectomy where a blade or other cutting element is used to sever and remove the atheroma, and laser angioplasty where laser energy is used to ablate at least a portion of the atheroma. Catheters can also be introduced to the vascular system for imaging, arrythmia mapping of the heart, defibrillation of the heart, and for a variety of other diagnostic procedures.

With all such techniques employing interventional and diagnostic catheters, it is necessary to properly locate the catheter so that the interventional or diagnostic element (usually at the distal tip of the catheter) is located at the region to be treated within the vascular system. As the catheters can be percutaneously introduced at locations quite remote from the region of atheroma, it is frequently necessary to maneuver and manipulate the catheter through various branches and regions within the vascular system.

One method for positioning vascular catheters utilizes guiding catheters. Such guiding catheters are elongated flexible tubes having a central lumen to accommodate the interventional or diagnostic vascular catheter to be introduced. Often, the guiding catheter will have a bent or curved tip to facilitate placement in a particular region of the vascular system, and positioning can be accomplished under conventional fluoroscopic imaging. Once the guiding catheter is in place, a diagnostic or imaging catheter can be introduced through the central lumen to the desired treatment location within the vascular system.

To be successful, the guiding catheter must satisfy a number of competing demands. The guiding catheter should be sufficiently flexible to permit introduction through the vascular system, particularly through the coronary arteries. The catheter should also be sufficiently axially rigid (i.e. have sufficient column strength) so that it can be pushed forward through the vascular system without kinking and collapse. Desirably, the catheter will have a controlled flexibility along its length to meet both these demands. The catheter should further have sufficient torsional stiffness so that the distal end can be turned (to properly orient the curved tip) by rotating the proximal end which remains accessible to the physician. The catheter should further have a relatively soft tip, to avoid injury to the blood vessel during initial placement. The catheter should still further be strengthened in the regions where it is curved or bent, as these regions are generally more prone to collapse. Catheter construction should also accommodate the placement of side holes or ports which permit perfusion of blood through the central lumen when the catheter is in place. Moreover, the catheter should be able to meet all of these mechanical demands while maximizing the cross-sectional area of the central lumen, i.e., minimizing wall thickness, to accommodate the interventional or diagnostic catheter, permit fluid infusion, and the like.

While previous guiding catheters have generally been able to meet at least some of these requirements, others have remained unmet. It would therefore be desirable to provide guiding catheters which meet at least most and preferably all of the above requirements with a minimum of compromise.

2. Description of the Background Art

U.S. Pat. No. 4,817,613, discloses a guiding catheter having an inner lubricous sleeve, a braided torque transmitting member, and a plastic material impregnated into the braided torque transmitting member. Other guiding catheters employing braided reinforcement layers are described in U.S. Pat. Nos. 4,425,919; 3,924,632; and 3,416,531; and Cook, Inc., Radiology, Cardiology, & Surgery Catalog (1982-84). The disclosures of each of these references is incorporated herein by reference.

Referring to FIGS. 1 and 2, a prior art guiding catheter 10 which has been commercially available from Devices for Vascular Intervention, Inc., assignee of the present application, includes a catheter body 12 constructed generally in accordance with U.S. Pat. No. 4,817,613, described above. The catheter body 12 includes an inner lubricous liner 14, a braided torque transmitting member 16, and a plastic material 18 impregnated into the torque transmitting member 16. A soft tip 20 extends over the distal approximately 2 mm of the inner lubricous liner 14 and lies adjacent to the termination of the braided layer 16. Side perfusion ports 22 are formed through the wall of the catheter body 12, penetrating the lubricous layer 14, the braided layer 16, and the impregnant layer 18. A stainless steel support ring 23 is provided in the region of the perfusion ports 22.

SUMMARY OF THE INVENTION

According to the present invention, a Vascular guiding catheter comprises an inner tubular member, a torque transmitting member disposed over the inner tubular member and extending from a proximal end thereof to a transition location spaced proximally inward from the distal end thereof, and a soft polymeric tip extending over the distal end of the inner tubular member. An outer layer impregnates the torque transmitting member and extends the entire length of the catheter until it meets the proximal end of the soft polymeric tip. Thus, there is a region between the termination of the torque transmitting member and the soft polymeric tip which includes both the inner tubular member and the outer tubular member, but which is free of the torque transmitting member.

In order to enhance axial rigidity of the distal end of the catheter and to form a smooth transition between the torque transmitting member and the soft distal tip, a reinforcement layer is formed at the distal end of the torque transmitting member and extends further over the inner tubular member. Such a reinforcement layer helps to maintain the desired shape of the distal region of the guiding catheter as well as to prevent cracking or collapse of the catheter at the critical transition between the torque transmitting member and the less stiff portions of the catheter distal to the torque transmitting member.

A central lumen of the inner tubular member will have a lubricous surface to facilitate introduction and removal of an interventional or imaging catheter (sometimes referred to as a working catheter) therethrough after the guiding catheter has been positioned in the vascular system. The torque transmitting member will have sufficient column strength and rotational stiffness so that the catheter can be advanced by pushing and turning from the proximal end without collapse. Usually, the torque transmitting member will comprise a braided tube and the outer layer comprises a polymeric material which impregnates the braid and has sufficient hardness to provide the desired strength characteristics. The transition region between the termination of the torque transition member and soft polymeric tip will be free from the braid and will include the reinforcement layer, as described above. The polymeric tip will be sufficiently soft and non-traumatic to minimize potential damage to the blood vessel as the catheter is being introduced, particularly to the ostium of the coronary artery. Preferably, the soft polymeric tip will be formed from a polymeric material having a hardness which is less than that of the polymer used to impregnate the braided tube of the torque transmitting member.

The reinforcement layer provides strain relief and inhibits collapse of the catheter at the transition junction between the torque transmitting member and the remainder of the catheter. The reinforcement layer also reduces the tendency for the relatively harder polymeric impregnant in the torque transmitting member to crack during use. The reinforcement layer will usually be a ring or sleeve of polymeric material formed over at least a portion of the distal end of the distal end of the torque transmitting member and over at least a portion of the inner tubular member which extends beyond the torque transmitting member.

In another preferred embodiment, one or more reinforcement layers may be provided over other regions of the torque transmitting member of the catheter, i.e., regions between the proximal end and the distal transition region. These reinforcement layers will find greatest use at curved and bent regions which are particularly susceptible to cracking and collapse during the introduction and manipulation of the catheter (particularly when curved regions are straightened). The provision of a relatively stiff reinforcement layer (i.e. harder than the polymeric impregnant material) will selectively enhance the strength of the catheter at these regions. The desired flexibility of the catheter in the remaining (usually straight) portions of the catheter, however, is not compromised. The reinforcement layers, however, may also be of use in straight regions of the catheter, particularly over straight regions which will be subjected to substantial bending and stress during use. Thermoplastic reinforcement layers will improve shape retention of the catheter and Will also permit selective shape modification by heating and reforming.

Preferred catheters of the present invention will usually include perfusion holes or ports formed within the region between the torque transmitting member and the soft polymeric tip. Such perfusion ports are desirable since they permit the bypass blood flow through the central lumen.

The guiding catheters of the present invention are thus able to satisfy most or all of the criteria set forth above. The catheters are sufficiently flexible to be introduced through a patient's vascular system, while remaining sufficiently strong so that they resist collapse and cracking when being introduced. In particular, the catheters have sufficient column strength and rotational stiffness to facilitate their introduction. The catheters will have a relatively soft tip to avoid traumatic injury to the blood vessel wall, while inclusion of the reinforcement layers helps the catheter retain its desired shape during use. The catheter construction will also accommodate side holes and ports suitable for blood perfusion.

DESCRIPTION OF THE SPECIFIC EMBODIMENT

Figure 1:
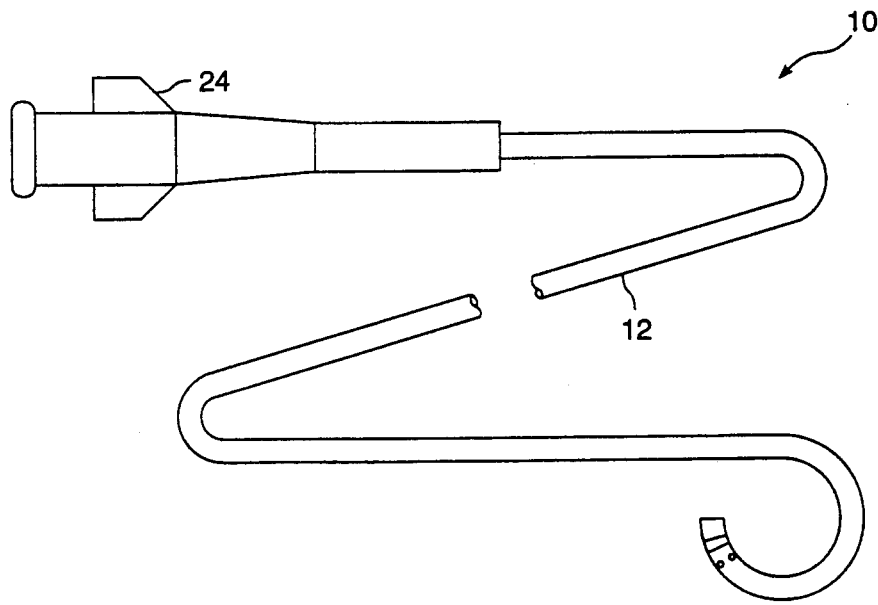
FIGS. 1 and 2 illustrate a prior art catheter as described in the Background of the Invention, above.
Figure 2:
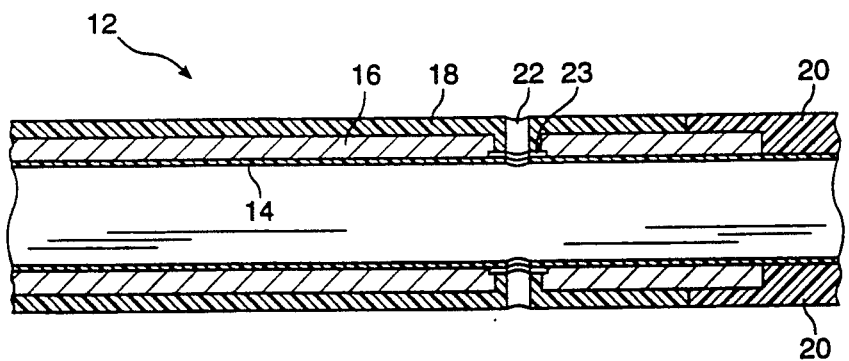

The present invention provides an improved vascular guiding catheter of the type which includes an elongated catheter body having a central lumen extending from a proximal end thereof to a distal end thereof and a proximal hub attached to said proximal end of the body. The proximal hub usually includes a conventional luer fitting which permits the introduction of a working catheter, such as an atherectomy catheter, an angioplasty catheter, a laser ablation catheter, an imaging catheter, a diagnostic catheter, or the like, to the central lumen after the catheter body has been positioned at a desired location within the vascular system. A typical winged hub 24 which may be used with the guiding catheters of the present invention is illustrated in FIG. 1.

The vascular guiding catheter of the present invention will have a shaped distal end including curves and bends which are selected to facilitate introduction and placement of the catheter within the vascular system. The particular curves and bends which are formed in the catheter body may be selected from a wide variety of conventional geometries which are well known in the art of making guiding catheters.

The catheter body will typically have a length in the range from about 50 cm to 150 cm, usually having a length in the range from about 90 cm to 110 cm. The diameter of the catheter body will typically be in the range from about 4 French (F; 1F=0.33 mm) to 12F, usually being the range from about 6F to 11F. The diameter of the central lumen will typically be in the range from about 3F to 11F, usually being from about 5F to 10F, with the larger catheters being sufficient to accommodate interventional and diagnostic catheters having a diameter up to at least 8F.

The catheter body includes an inner tubular member which defines the central lumen and provides a lubricous surface to receive the interventional or diagnostic catheter with minimum friction. Typically, the inner tubular member will be a sleeve formed from a single material, preferably a lubricous polymer, such as a fluorocarbon (e.g., polytetrafluoroethylene (PTFE)), a polyamide (e.g., nylon), a polyolefin, polyimide, or the like. It would also be possible to form the inner tubular member as a laminate structure with only an inner layer formed from a lubricous material.

The catheter body further includes a torque transmitting member disposed over the inner tubular member and extending from a proximal end of the inner tubular member to a transition location spaced proximally inward from the distal end of the inner tubular member. The torque transmitting member may itself be a tube or sleeve having a uniform or homogeneous structure, but will preferably be a laminate structure comprising at least a single braided layer impregnated with a polymeric material (defining an outer layer) to achieve desired mechanical and structural characteristics. In particular, the torque transmitting member will provide sufficient torsional stiffness so that rotation of the proximal end of the catheter body will cause rotation of the distal end so that the treating physician can manipulate the curved tip to guide the catheter through the bends and branches of the vascular system. The catheter body will also be sufficiently flexible in the axial direction (i.e. have a sufficiently low axial bending stiffness) to support passage and tracking of the catheter through the vascular system. The axial flexibility (or axial bending stiffness) may vary over the length of the catheter body, with a relatively greater stiffness being acceptable near the proximal end. The preferred construction of catheter bodies having a controlled stiffness and comprising braided layers impregnated with a polyurethane impregnant are described in detail in U.S. Pat. No. 4,817,613, the full disclosure of which has previously been incorporated herein by reference.

The present invention provides improvement over the catheter body described in U.S. Pat. No. 4,817,613. In particular, the catheter body of the present invention will comprise a soft polymeric tip member disposed over the inner tubular member and extending in the distal direction from the distal end of the torque transmitting member to the distal end of the inner tubular member. The soft polymeric tip will be formed from a polymeric material having a hardness which is less than the polymer used as an impregnant to form the outer layer over the remainder of the catheter body. In particular, the polymeric material which is used as the impregnant will typically have a hardness in the range from about 40 Shore D to 90 Shore D, usually being in the range from about 50D to 80D and preferably being in the range from about 60D to 70D. The polymer of the soft polymeric tip will have a hardness in the range from about 40 Shore A to 90 Shore A, usually in the range from about 50A to 80A, and preferably in the range from about 60A to 70A. In all cases, the soft polymeric tip will be free from braid and other reinforcement layers which might stiffen the tip and increase the chance that it could cause injury when the catheter is being introduced to the vascular system.

The soft polymeric tip may be formed from a variety of polymeric materials, usually being formed from a polyurethane, and preferably being formed from a thermoplastic polyurethane. A suitable polyurethane is TU700, available from Conap, Inc. Olean, N.Y.

The length of the soft polymeric tip will be sufficient to provide adequate cushioning at the distal tip of the catheter. Usually, the soft polymeric tip will have a length in the range from about 0.5 mm to 8 mm, more usually in the range from about 1 mm to 5 mm, and preferably in the range from about 1 mm to 3 mm. The outer diameter of the soft polymeric tip will generally be approximately the same as the remainder of the catheter body, i.e. the torque transmitting member, but there is no reason why the diameter could not be somewhat larger or smaller.

Conveniently, one or more perfusion ports will be formed through the region between the termination of the torque transmitting member and the soft polymeric tip of the catheter body to provide for bypass flow of blood when the guiding catheter is in place during a procedure. Perfusion ports which are formed through this region are generally cleaner than those which are formed through a braided reinforcement layer. In particular, perfusion ports formed through a braided reinforcement layer are subject to the presence of burrs and other irregularities which can be thrombogenic and which could subject the blood vessel wall to injury. Such irregularities can also damage an interventional or diagnostic catheter which is introduced.

The guiding catheters of the present invention will further comprise one or more reinforcement layers disposed at or over particular regions in order to provide strain relief, enhance shape retention, inhibit cracking or collapse, and/or permit reshaping of the catheter. The reinforcement layers will usually be at least partly impregnated into the torque transmitting member, more usually being a thermoplastic material which is melted into a braided torque transmitting member. Such reinforcement layers will be composed of a polymeric material having a hardness which differs from that of the impregnant which forms the outer layer, usually being harder to provide enhanced stiffness and collapse resistance. Thus, the hardness of the reinforcement layer material will be in the range from 50D to 100D, usually being from 60D to 90D.

The reinforcement layer will usually be composed of a deformable polymeric material having a relatively high elongation constant. Preferably, the material will have an elongation constant in the range from about 100% to 400%, usually being in the range from about 200% to 300%, and most often in the range from 240% to 260%. An exemplary material for the reinforcement material is Nylon 12. Other suitable materials include polyurethanes, polyamides, polyethylene terephthalates, and the like. Reinforcement layers may be formed by molding, shrink wrapping, or other conventional techniques over the reinforcement layer and/or the inner tubular member.

In a particular aspect, a reinforcement layer is formed over the transition between the distal termination of the torque transmitting member and the distal portions of inner tubular member. The transition reinforcement layer will have a length from about 1 mm to 1 cm, usually from 2 mm to 5 mm, and will extend over both the torque transmitting member and the inner tubular member.

In a second particular aspect, one or more reinforcement layers may be formed over or beneath the torque transmitting member in regions between the proximal end thereof and the transition region. By "over" it is meant that the reinforcement layer will be initially placed on the outer surface of the torque transmitting member and impregnated at least partly into the torque transmitting member before the outer layer is impregnated or otherwise formed over the catheter. By "beneath" it is meant that the reinforcement layer will be initially placed between the outer surface of the inner tubular member and the inner surface of the torque transmitting member. After the torque transmitting member is in place, the reinforcement layer can be melted to cause impregnation of the torque transmitting member from below.

Reinforcement layers disposed proximally of the transition region will be used to reinforce regions of particular stress, particularly including curved regions of the catheter which will be straightened as the catheter is introduced and straight regions of the catheter which will be subjected to particularly sharp bending as the catheter is introduced. The length of these reinforcement layers will usually be from several centimeters to 50 cm, or larger, and in some cases it may be desirable to apply the reinforcement layer over the entire length of the catheter.

In a third aspect, the reinforcement layers may be formed from a thermoplastic, such as nylon or a thermoplastic polyurethane, which permits reshaping of the catheter by heating and reforming of the reinforcement layer. When reshaping is not a requirement, the reinforcement layer may be formed from a thermosetting polymer.

In a fourth aspect, the bending stiffness of the catheter at different locations along its length can be selectively modified by forming reinforcement layers having differing hardness. For example, relatively stiff regions can be formed by incorporating a reinforcement layer having a hardness in the range from 60D to 100D, usually from 65D to 90D. Less stiff regions can be formed by incorporating a softer reinforcement layer having a hardness in the range from 50D to 70D, usually from 50D to 60D.

Figure 3:
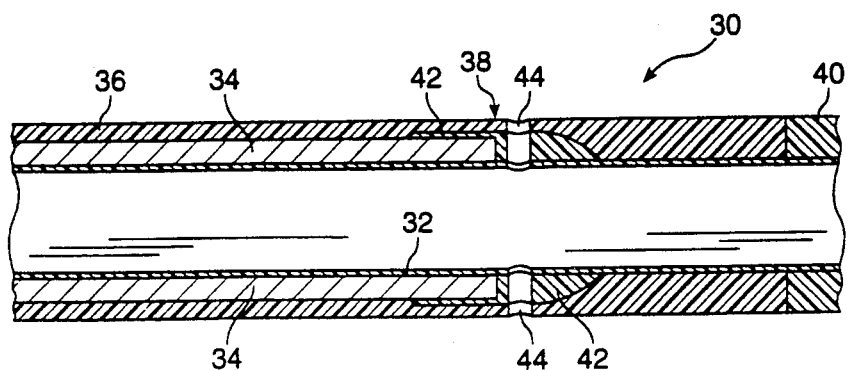
FIG. 3 is a side elevational view of the distal tip of a guiding catheter constructed in accordance with the principles of the present invention.

Referring now to FIG. 3, the distal end 30 of an exemplary catheter 30 constructed in accordance with the principles of the present invention is illustrated. The proximal portions of the catheter (i.e., those which are not illustrated) may be of conventional construction, for example in accordance with the teachings of U.S. Pat. No. 4,817,613, the disclosure of which has previously been incorporated herein by reference. Guiding catheter 30 comprises an inner tubular member 32, a torque transmitting member 34 (typically a braided layer as described above), disposed over a portion of the inner tubular member 32, and an outer layer 36 extending over the torque transmitting member and the inner tubular member. The torque transmitting member 34 terminates at a transition region 38, where the portion of the catheter 30 lying distally of the transition region has substantially different mechanical properties since it is free of the torque transmitting member. The catheter 30 terminates at its distal tip in a soft polymer tip member 40.

A reinforcement layer 42 extends across the distal end of the torque transmitting member 34 and onto inner tubular member 32 to cover and provide strain relief at the transition region 38. The reinforcement layer 42 has the mechanical properties described above and provides strain relief between the termination of the relatively stiff torque transmitting member an the much less stiff distal portion of the catheter 30. Conveniently, side perfusion ports 44 may be formed through the side wall of the guiding catheter 30 within the region which is free from the torque transmitting member 34 but which is reinforced by reinforcement layer 42. In this way, relatively clean perfusion ports may be formed which are substantially free from burrs and irregularities. Moreover, the tendency of the perfusion ports to weaken the side wall of the catheter 30 (and thus increase the chance that the catheter will collapse and/or crack in this region), is greatly reduced.

In a preferred aspect of the present invention, the space between the torque transmitting member 32 and the soft polymeric tip 40 will be formed from substantially clear or partially translucent polymeric materials to improve the ability to inspect the final manufactured structure.

In another preferred aspect of the present invention, one or more radiopaque bands will be formed at or near the distal tip of the catheter, particularly at or near the soft polymeric tip 40.

Figure 4:
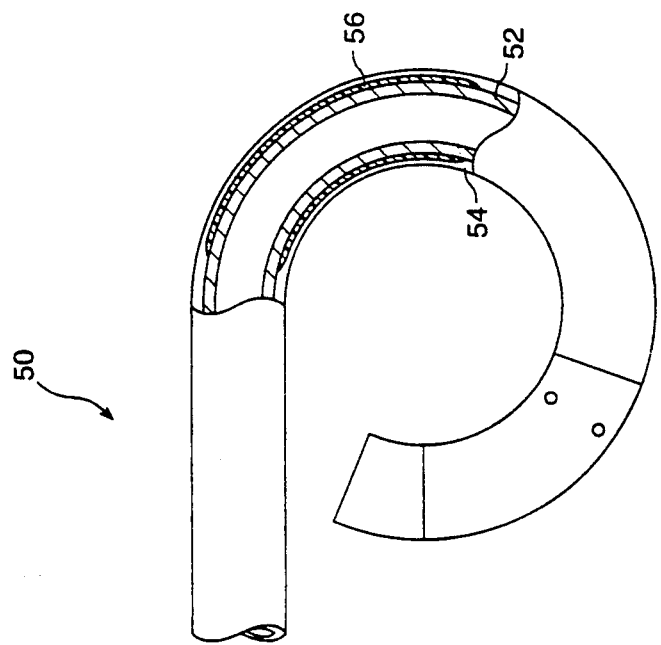
FIG. 4 is a side elevation view of a distal portion of a guiding catheter constructed in accordance with the principles of the present invention with portions broken away and illustrated in cross-section.
Figure 4:
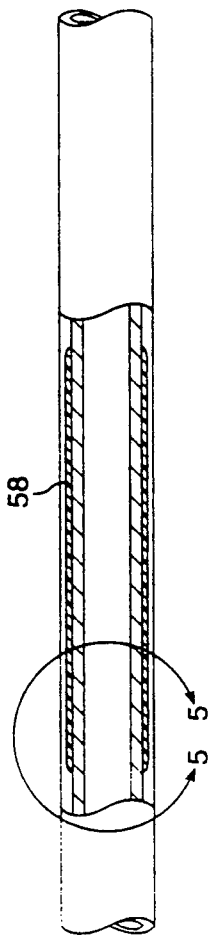
Figure 5:
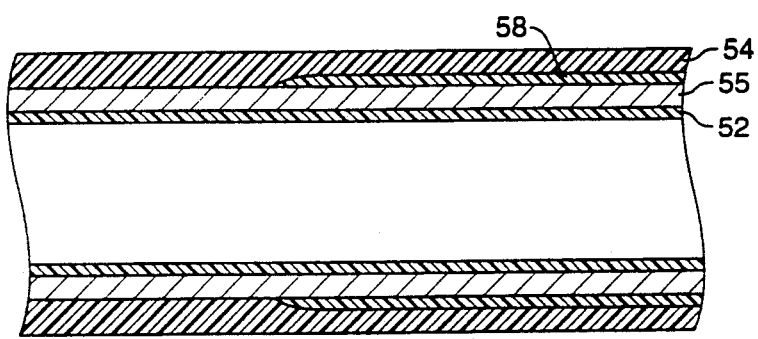
FIG. 5 is an enlarged cross-sectional view of a portion of the catheter of FIG. 4 illustrated at line 5—5.

Referring now to FIGS. 4 and 5, use of the reinforcement layers of the present invention to strengthen the catheter construction over proximal portions of a guiding catheter 50 will be described. The guiding catheter 50 includes a curved region at its distal end, including an inner tubular member 52 and an outer layer 54, constructed as described above. In order to help maintain the desired curved geometry of the catheter, as well as to help resist collapse and cracking of the catheter when the curved region is straightened during use, a polymeric reinforcement layer 56 may be impregnated into the torque transmitting member, as described above.

A similar reinforcement layer 58 may be formed over straight portions of the catheter 50, particularly when it is expected that the straight portion will undergo substantial bending during use, where the bending might contribute to collapse and cracking of the catheter.

The detailed structure of the inner tubular member 52, outer layer 54, torque transmitting member 55, and the reinforcement layer 58 is better observed in FIG. 5. The reinforcement layers 56 and 58 will preferably be applied as a preformed ring or sleeve of extruded material, e.g. Nylon-12, over the exterior of the torque transmitting member 55. The sleeve is then heated, causing the material to flow into the braided layer(s) of the torque transmitting member. Conveniently, a heat shrinkably Teflon ® or other material cylinder is placed over the sleeve of reinforcement material to apply uniform pressure as the heat is applied. Optionally, the structure may be rotated to further enhance the uniformity of impregnation. Additionally (or alternatively), the reinforcement material may be applied between the exterior surface of the inner tubular member 52 and the interior surface of the torque transmitting member 55. In this way, the reinforcement material may impregnate the torque transmitting member in a radially outward direction.

Although the foregoing invention has been described in detail for purposes of clarity of understanding, it will be obvious that certain modifications may be practiced within the scope of the appended claims.

What is claimed is:

1. A guiding catheter comprising;
    an inner tubular member having a proximal end, a distal end, and central lumen extending from the proximal end to the distal end, wherein said lumen has a lubricous surface for receiving an interventional or diagnostic catheter;
    a torque transmitting member including a braided tubular structure disposed over the inner tubular member and extending from the proximal end thereof to a transition location spaced proximally inward from the distal end thereof;

a reinforcement layer composed of a polymeric material extending over at least a portion of the distal end of the torque transmitting member and over at least a portion of the inner tubular member which extends beyond the torque transmitting member; and an outer layer including a polymeric material having a hardness in the range from 40D to 90D extending over the torque transmitting member and impregnating the tubular structure, the reinforcement layer, and any portion of the inner tubular member which extends beyond the reinforcement layer.

2. A guiding catheter as in claim 1, wherein the braided tubular structure includes at least one layer composed of stainless steel braid.

3. A guiding catheter as in claim 1, wherein the polymeric material is a polyurethane.

4. A guiding catheter as in claim 1, wherein the outer layer terminates at its distal end in a soft polymeric tip having a hardness in the range from 40A to 90A, said soft tip extending over the distal 0.5 mm to 8 mm of the guiding catheter.

5. A guiding catheter as in claim 4, wherein the soft polymeric tip is composed of a polyurethane.

6. A guiding catheter as in claim 4, wherein the reinforcement layer is composed of a material which is harder than the material of the outer layer.

7. A guiding catheter as in claim 6, wherein the reinforcement layer is composed of a polymeric material having a hardness in the range from about 50D to 100D.

8. A guiding catheter as in claim 1, further comprising at least one additional reinforcement comprising a reinforcement layer impregnated within at least a portion of the torque transmitting member proximal to the transition location.

9. A guiding catheter as in claim 8, wherein the additional reinforcement layer is composed of a polymeric material having a hardness in the range from about 50D to 100D.

10. A guiding catheter as in claim 2, wherein the additional reinforcement layer is formed over the torque transmitting member.

11. A guiding catheter as in claim 1, including at least two additional reinforcement segments, said additional reinforcement segments being axially spaced apart and disposed over the torque transmitting member within the outer layer, said outer layer occupying the space between said additional reinforcement segments.

12. A guiding catheter as in claim 11, wherein the at least two reinforcement segments have different hardnesses to form regions on the catheter having different bending stiffnesses.

13. A guiding catheter as in claim 1, having side ports located distally of the transition location.

14. A guiding catheter as in claim 13, wherein the side ports penetrate through the reinforcement layer.

15. A guiding catheter as in claim 1, further comprising at least one radiopaque band formed distally on the transition region.

16. An improved guiding catheter of the type including an inner tubular member running substantially the full length of the catheter, a braided torque transmitting member disposed over the inner tubular member, and an outer polymeric layer impregnating the braided torque transmitting member, wherein the improvement comprises at least one reinforcement segment impregnating the braided torque transmitting member and displacing the outer polymeric layer from a position of the braided torque transmitting member, wherein the reinforcement segment has a length less than that of the inner tubular member and wherein the reinforcement segment has a hardness which is greater than that of the outer polymeric layer.

17. An improved guiding catheter as in claim 16, wherein the reinforcement segment is disposed over a curved region of the catheter.

18. An improved guiding catheter as in claim 16, wherein the reinforcement segment is disposed over a straight region of the catheter.

19. An improved catheter as in claim 16, wherein the outer polymeric layer has a hardness from 40D to 90D and the reinforcement segment has a hardness from 50D to 100D.

20. A guiding catheter comprising:

an inner tubular member having a proximal end, a distal end, and a central lumen extending from the proximal end to the distal end, wherein said lumen has a lubricous surface for receiving an interventional or diagnostic catheter;

a torque transmitting member disposed over the inner tubular member and extending from the proximal end thereof to a transition location spaced proximally inward from the distal end thereof;

a reinforcement layer composed of a polymeric material extending over at least a portion of the distal end of the torque transmitting member and over at least a portion of the inner tubular member which extends beyond the torque transmitting member;

an outer layer extending over the torque transmitting member, the reinforcement layer, and any portion of the inner tubular member which extends beyond the reinforcement layer; and at least one additional reinforcement segment comprising a reinforcement layer impregnated within at least a portion of the torque transmitting member proximal to the transition location.

21. A guiding catheter as in claim 20, wherein the torque transmitting member includes a braided tubular structure and the outer layer includes a polymeric material having a hardness in the range from 40D to 90D, said polymeric material impregnating the braided tubular structure.

22. A guiding catheter as in claim 21, wherein the braided tubular structure includes at least one layer composed of stainless steel braid.

23. A guiding catheter as in claim 21, wherein the polymeric material is a polyurethane.

24. A guiding catheter as in claim 20, wherein the outer layer terminates at its distal end in a soft polymeric tip having a hardness in the range from 40A to 90A, said soft tip extending over the distal 0.5 mm and 8 mm of the guiding catheter.

25. A guiding catheter as in claim 24, wherein the soft polymeric tip is composed of a polyurethane.

26. A guiding catheter as in claim 24, wherein the reinforcement layer is composed of a material which is harder than the material of the outer layer.

27. A guiding catheter as in claim 26, wherein the reinforcement layer is composed of a polymeric material having a hardness in the range from about 50D to 100D.

28. A guiding catheter as in claim 20, wherein the additional reinforcement layer is composed of a polymeric material having a hardness in the range from about 50D to 100D.

29. A guiding catheter as in claim 28, including at least two additional reinforcement segments, said additional reinforcement segments being axially spaced apart and disposed over the torque transmitting member within the outer layer, said outer layer occupying the space between said additional reinforcement segments.

30. A guiding catheter as in claim 29, wherein the at least two reinforcement segments have different hardnesses to form regions on the catheter having different bending stiffnesses.

31. A guiding catheter as in claim 20, wherein the additional reinforcement layer is formed over the torque transmitting member.

32. A guiding catheter as in claim 20, wherein the additional reinforcement layer is formed between the torque transmitting member and the inner tubular member.

33. A guiding catheter as in claim 20, having side ports located distally of the transition location.

34. A guiding catheter as in claim 33, wherein the side ports penetrate through the reinforcement layer.

35. A guiding catheter as in claim 20, further comprising at least one radiopaque band formed distally of the transition region.

* * * * *